United States Patent
Anderson et al.

(10) Patent No.: US 6,821,975 B1
(45) Date of Patent: Nov. 23, 2004

(54) BETA-CARBOLINE DRUG PRODUCTS

(75) Inventors: Neil R. Anderson, West Lafayette, IN (US); Kerry J. Hartauer, Carmel, IN (US); Martha A. Kral, Indianapolis, IN (US); Gregory A. Stephenson, Fishers, IN (US)

(73) Assignee: Lilly ICOS LLC, Wilmington, DE (US)

( * ) Notice: Subject to any disclaimer, the term of this patent is extended or adjusted under 35 U.S.C. 154(b) by 110 days.

(21) Appl. No.: 10/031,463

(22) PCT Filed: Aug. 1, 2000

(86) PCT No.: PCT/US00/20981

§ 371 (c)(1),
(2), (4) Date: Jul. 19, 2002

(87) PCT Pub. No.: WO01/08688

PCT Pub. Date: Feb. 8, 2001

Related U.S. Application Data

(60) Provisional application No. 60/147,048, filed on Aug. 3, 1999.

(51) Int. Cl.$^7$ .................. A61K 31/4985; C07D 405/14
(52) U.S. Cl. ........................................ 514/250; 544/343
(58) Field of Search .......................... 544/343; 514/250

(56) References Cited

U.S. PATENT DOCUMENTS

| | | | |
|---|---|---|---|
| 5,859,006 A | 1/1999 | Daugan |
| 5,985,326 A | 11/1999 | Butler |

FOREIGN PATENT DOCUMENTS

| | | |
|---|---|---|
| GB | 2293103 | 3/1996 |
| WO | WO 96/38131 | 12/1996 |
| WO | 01/08686 A1 * | 2/2001 |
| WO | 01/08687 A1 * | 2/2001 |

* cited by examiner

*Primary Examiner*—Emily Bernhardt
(74) *Attorney, Agent, or Firm*—Marshall, Gerstein & Borun LLP

(57) ABSTRACT

A compound of structural formula (I), and pharmaceutically acceptable salts and solvates thereof, wherein the compound is in free drug particulate form, is disclosed.

11 Claims, 1 Drawing Sheet

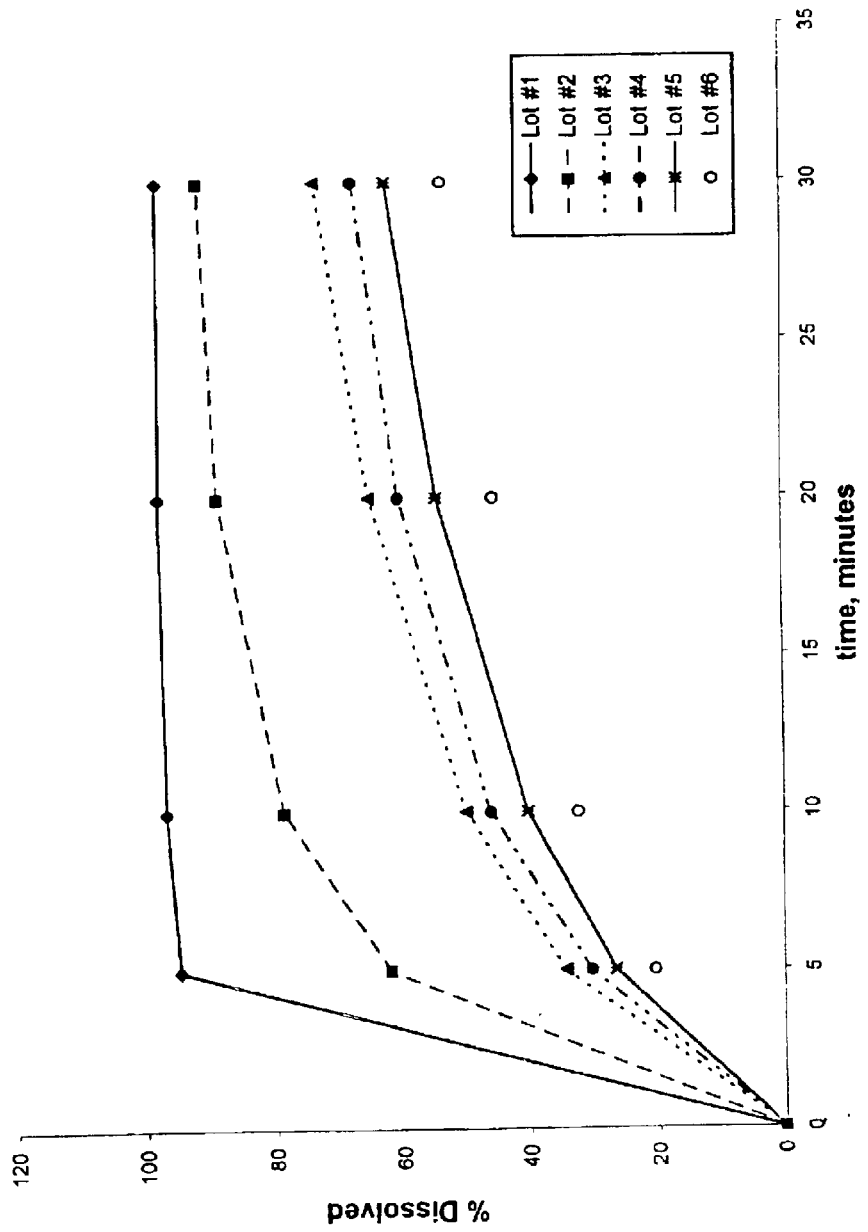
Figure 1. Comparison of Bulk Drug Substance Dissolution Profiles

BETA-CARBOLINE DRUG PRODUCTS

CROSS-REFERENCE TO RELATED APPLICATION

This is the U.S. national phase application of International Application No. PCT/US00/20981, filed on Aug. 1, 2000, which claims the benefit of provisional patent application Ser. No. 60/147,048, filed Aug. 3, 1999.

FIELD OF THE INVENTION

The present invention relates to the fields of pharmaceutical and organic chemistry, and to a β-carboline compound which is useful for the treatment of various medical indications where inhibition of type 5 cGMP-specific phosphodiesterase (PDE5) is desired. More particularly the present invention provides a free drug form of β-carboline particles in a size range allowing for uniform formulation of stable pharmaceutical compositions, especially compositions providing desired bioavailability properties heretofore not provided in the art.

BACKGROUND OF THE INVENTION

The biochemical, physiological, and clinical effects of cyclic guanosine 3',5'-monophosphate specific phosphodiesterase (cGMP-specific PDE) inhibitors suggest their utility in a variety of disease states in which modulation of smooth muscle, renal, hemostatic, inflammatory, and/or endocrine function is desired. Type 5 cGMP-specific phosphodiesterase (PDE5) is the major cGMP hydrolyzing enzyme in vascular smooth muscle, and its expression in penile corpus cavernosum has been reported (Taher et al., J. Urol., 149:285A (1993) ). Thus, PDE5 is an attractive target in the treatment of sexual dysfunction (Murray, DN&P 6(3): 150–156 (1993)).

Daugan U.S. Pat. No. 5,859,006 discloses a class of β-carboline compounds, and pharmaceutical compositions containing the β-carbolines, which are useful in the treatment of conditions wherein inhibition of PDE5 is desired. PCT publication WO 97/03675 discloses use of this class of β-carboline compounds in the treatment of sexual dysfunction.

The poor solubility of many β-carboline compounds useful as PDE5 inhibitors prompted the development of coprecipitate preparations, as disclosed in PCT publication WO 96/38131 and Butler U.S. Pat. No. 5,985,326. Briefly, coprecipitates of a β-carboline with polymeric hydroxypropylmethylcellulose phthalate, for example, were prepared, milled, mixed with excipients, and compressed into tablets for oral administration. Studies revealed, however, that difficulties arose in generating precisely reproducible lots of coprecipitate product, which makes use of coprecipitates less than ideal in pharmaceutical formulations.

Additionally, clinical studies involving administration of coprecipitate tablets preliminarily revealed that maximum blood concentration of the β-carboline compound is achieved in 3 to 4 hours, with the average time for onset of therapeutic effect not yet precisely determined. In the treatment of sexual dysfunction, such as male erectile dysfunction or female sexual arousal disorder, however, a more rapid achievement of maximum blood concentration, along with a greater prospect for rapid onset of therapeutic effect, frequently is sought by individuals desiring more immediate and/or less prolonged effects. Accordingly, a need in the art continues to exist for orally administrable β-carboline compounds and 5-carboline-containing pharmaceutical compositions having an ability to provide a therapeutic effect within a desirable, or at least acceptable, time frame.

SUMMARY OF THE INVENTION

The present invention provides particulate preparations of a free drug form of a β-carboline compound having specific and defined particle size characteristics. The defined particle size permits a uniform formulation of stable pharmaceutical compositions. In particular, the present invention provides compositions that exhibit a rapid achievement of maximum blood concentration of PDE5 inhibitor and/or a rapid onset of a therapeutic PDE5 inhibitory effect.

The present invention provides a compound having the formula (I)

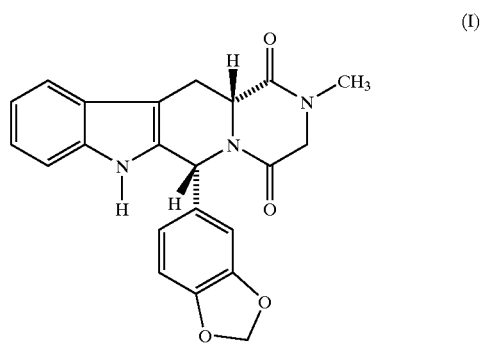

(I)

and pharmaceutically acceptable salts and solvates thereof, wherein the compound is a free drug in particulate form, and wherein at least 90% of the particles have a particle size of less than about 40 microns, and preferably less than 30 microns. Highly preferred particulate forms of the β-carboline compound (I) have at least 90% of the particles less than 25 microns in size. Most preferred forms of the free compound (I) are those wherein 90% of the particles are less than 10 microns in size.

The present invention provides, therefore, a free form of a β-carboline compound, and compositions containing the β-carboline compound, which can be used in an effective therapy for conditions wherein inhibition of PDE5 provides a benefit. The free form of β-carboline compound (I) has a particle size such that the onset of beneficial effects of PDE5 inhibition are exhibited in a relatively short time after oral administration.

The present invention further relates to pharmaceutical compositions comprising the particulate compound (I) and one or more pharmaceutically acceptable carriers, diluents, or excipients. The invention further provides the use of compound (I) and pharmaceutical compositions for treatment of sexual dysfunction, e.g., male erectile dysfunction and female sexual arousal disorder.

Alternatively stated, the present invention provides for the use of the above-described particulate forms of compound (I) for the manufacture of medicaments for the treatment of sexual dysfunction Specific conditions that can be treated by the compound and compositions of the present invention include, but are not limited to, male erectile dysfunction and female sexual dysfunction, for example, female arousal disorder, also known as female sexual arousal disorder.

Accordingly, one aspect of the present invention is to provide a free drug particulate form of a compound (I), and pharmaceutically acceptable salts and solvates thereof, comprising particles of the compound wherein at least 90% of the particles have a particle size of less than about 40 microns.

Another aspect of the present invention is to provide a pharmaceutical composition comprising particles of the free drug particulate form of compound (I) having a d90 less than 40, and one or more pharmaceutically-acceptable carriers, diluents, or excipients, and a method of manufacturing the composition.

Yet another aspect of the present invention is to provide a method of treating sexual dysfunction in patients in need thereof comprising administering to a patient in need thereof a therapeutically effective amount of a composition comprising particles of the free drug particulate form of compound (I) having a d90 less than 40 and one or more pharmaceutically-acceptable carriers, diluents, or excipients. The sexual dysfunction can be male erectile dysfunction or female arousal disorder, for example.

Still another aspect of the present invention is to provide a pharmaceutical composition comprising: (a) a free drug form of compound (I), and pharmaceutically-acceptable salts and solvates thereof, and (b) one or more pharmaceutically-acceptable carriers, diluents, or excipients, wherein the composition exhibits a $C_{max}$ of about 180 to about 280 micrograms/liter or an AUC (0–24) of about 2280 to about 3560 microgram hour/ liter, measured using a 10 milligram dose of the compound. The composition can be a solid, a suspension, or a solution.

Another aspect of the present invention is to provide a pharmaceutical composition comprising: (a) compound (I) and pharmaceutically-acceptable salts and solvates thereof, and (b) one or more pharmaceutically-acceptable carriers, diluents, or excipients, wherein the composition exhibits a $C_{max}$ of about 180 to about 280 micrograms/liter and an AUC (0–24) of about 2280 to about 3560 micrograms hour/liter, measured using a 10 milligram dose of the compound. The composition can be a solid or a suspension.

Another aspect of the present invention is to provide a pharmaceutical composition comprising: (a) a free drug form of compound (I), and pharmaceutically acceptable salts and solvates thereof, wherein at least 90% of the particles have a particle size of less than about 10 microns, and (b) one or more pharmaceutically-acceptable carriers, diluents, or excipients, and bioequivalent compositions thereof. The composition can be a solid or a suspension.

These and other aspects of the present invention will become apparent form the following detailed description of the invention.

BRIEF DESCRIPTION OF THE DRAWINGS

FIG. 1 contains plots of % of dissolved compound (I) vs. time, and illustrates the in vitro dissolution characteristics of compound (I) in a varying particle size.

DETAILED DESCRIPTION OF INVENTION

For purposes of the claimed invention as disclosed and described herein, the following terms and abbreviations are defined as follows.

The term "treatment" includes preventing, lowering, stopping, or reversing the progression or severity of a condition or symptoms being treated. As such, the present invention includes both therapeutic and prophylactic administration, as appropriate.

The term "effective amount" is an amount of compound (I), or a composition containing compound (I), that is effective in treating the condition or symptom of interest. An effective amount of a compound (I) to treat sexual dysfunction in a male is an amount sufficient to provide and sustain an erection capable of penetrating the partner. An effective amount of a compound (I) to treat female sexual dysfunction, particularly female sexual arousal disorder, is an amount sufficient to enhance the ability of a female to achieve or sustain an aroused state.

The term "free drug" refers to solid particles of compound (I) not intimately embedded in a polymeric coprecipitate.

The term "suspension" refers to a liquid composition containing free drug particles of compound (I). The term "solution" refers to a liquid composition having compound (I) dissolved therein.

The term "solvate" comprises one or more molecules of compound (I) associated one or more molecule of a solvent, e.g., water or acetic acid.

The term "oral dosage form" is used in a general sense to refer to pharmaceutical products administered via the mouth. Solid oral dosage forms are recognized by those skilled in the art to include such forms as tablets, capsules, and aerosols.

The term "pharmaceutically acceptable" means carriers, excipients, diluents, salt forms of compound (I), and other formulation ingredients that are compatible with all other ingredients of a composition, and are not deleterious to an individual treated with the composition.

The nomenclature describing the particle size of compound (I) is commonly referred to, and is herein, as the "d90." For example, a d90 of 40 (or d90=40) means that at least 90% of the particles have a particle size of less than 40 microns.

As noted, the present invention provides a compound of structural formula (I), and pharmaceutically acceptable salts and solvates thereof, characterized in that the compound is a free drug in particulate form, wherein at least 90% of the particles have a particle size of less than about 40 microns.

It has been found that by processing (6R-trans)-6-(1,3-benzodioxol-5-yl)-2,3,6,7,12,12a-hexahydro-2-methylpyrazino[1',2':1,6]pyrido[3,4-b]indole-1,4-dione, alternatively named (6R, 12aR)-2,3,6,7,12,12a-hexahydro-2-methyl-6-(3,4-methylene-dioxyphenyl)pyrazino[2',1':6.1]pyrido[3,4-b]indole-1,4-dione, as disclosed in Daugan U.S. Pat. No. 5,859,006, and represented by structural formula

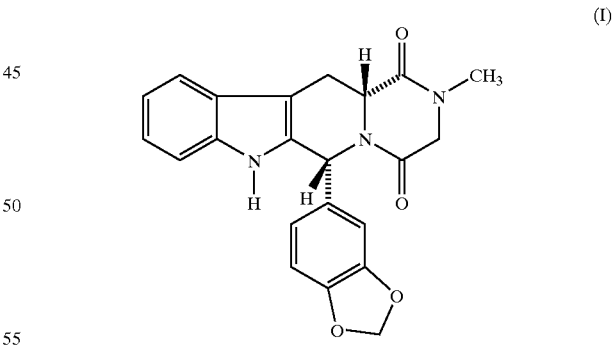

to bring the particle size within a particular narrow range, manufacturing capability is enhanced, and pharmaceutical compositions can be prepared that exhibit an improved bioavailability of the active ingredient, i.e., compound (I).

The present invention encompasses particles of free compound (I) wherein at least 90% of the particles of free drug have a particle size of less than about 40 microns (i.e., d90=40), and preferably less than 30 microns. More preferably, at least 90% of the particles have a particle size of less than 25 microns, still more preferably less than 15 microns, and to achieve the full advantage of the present invention, d90 is less than 10 microns. Particles having a d90 in the nanometer range (e.g., about 200 nm or less, or about 50 nm or less) also are contemplated. However, nanometer sized particles of compound (I) are difficult to handle and to formulate, and tend to aggregate. Therefore, a preferred d90 range for the particles of free compound (I) is about 1 to about 40 microns.

Preferably, the free drug is crystalline. However, amorphous and partially amorphous forms of compound (I) also are contemplated, and are included within the present invention.

It is understood by those familiar with comminution process techniques that the limit set on the size of 90% or more of the particles, using normal milling techniques, is a feature to further distinguish the particulate compounds of the invention from particles exhibiting a broader size distribution. Because of the variation in size encountered in all matter reduced in size by a comminution process, expressing differences in particle size in the manner described herein is readily accepted by those skilled in the art.

The present invention also provides pharmaceutical compositions comprising said particulate compound (I) and one or more pharmaceutically acceptable excipients, diluents, or carriers. The excipient, diluent, or carrier can be a solid component of the composition or a liquid component. Accordingly, pharmaceutical compositions containing particles of free compound (I) can be a solid composition, or can be a suspension of free compound (I) particles in a liquid excipient, diluent, or carrier.

The compound of the structural formula (I) can be made according to established procedures, such as those detailed in U.S. Pat. No. 5,859,006, incorporated herein by reference. The preparation of the compound of structural formula (I) is specifically provided in U.S. Pat. No. 5,859,006.

Methods of determining the size of particles are well known in the art. For example, the general method of U.S. Patent No. 4,605,517, incorporated herein by reference, could be employed. The following is a description of one nonlimiting method.

In preparing the particulate compound of the present invention, a compound of structural formula (I), in its raw state, first is characterized for size using an instrument adapted to measure equivalent spherical volume diameter, e.g., a Horiba LA910 Laser Scattering Particle Size Distribution Analyzer or equivalent instrument. Typically, a representative sample of a compound of structural formula (I) is expected to comprise, in its raw 5 state, particles having a d90 equivalent spherical volume diameter of about 75 to about 200 microns, and with a broad size distribution.

After being characterized for size in its raw state, the free drug compound then is milled, for example using a pin mill under suitable conditions of mill rotation rate and feed rate, to bring the particle size value within the above mentioned limits of the present invention. The efficiency of the milling is monitored by sampling, using a Horiba LA910 Laser Scattering Particle Size Distribution Analyzer, and the final particle size is confirmed in a similar manner. If a first pass through the mill fails to produce the required size distribution, then one or more further passes are effected. Other methodologies to prepare particles as described herein are readily available, including a variety of milling techniques, such as hammer or fluid energy mills.

The particles of compound (I) in the raw state, as well as after milling or other particle size reduction techniques, are irregular in shape. Therefore, it is necessary to characterize the particles by a measurement different from actual size, like thickness or length, for example, by measurement of a property, like intensity and angle of diffracted light, and equate that measurement to the diameter of known spherical particles having the measured same property. The particles are thus allocated an "equivalent spherical diameter." The values found from characterizing a large number of "unknown" particles can be plotted as cumulative frequency vs. diameter, or in other methods weight vs. diameter, usually adopting percentage undersize values for cumulative frequency or weight. This provides a characteristic curve representing size distribution of the sample, i.e., cumulative percentage undersize distribution curve. Values can be read directly from the curve, or, alternatively, the measurements are plotted on log-probability paper to give a straight line, and the values can be read therefrom.

The d90 equivalent spherical volume diameter thus found is a statistical representation of the 90% point on a cumulative frequency plot. As indicated, the d90 equivalent sphere volume diameter of the particles of the milled compound of formula (I) are evaluated using a Horiba LA910 Laser Scattering Particle Size Distribution Analyzer or other such equipment recognized by those skilled in the art. Using such instrument values for a suspension of the particles of unknown size are obtained, and the instrument is monitored using a contro sample having particles within the size range expected based on statistical analysis of the control sample.

The particle size of compound (I) prior to formulation into a pharmaceutical composition can be measured, for example, as follows. The laser scattering particle size distribution analysis is effected on a small sample of the reduced material, which is suspended in approximately 180 ml of dispersant solution. Prior to sample suspension, a dispersant solution containing 0.1% SPAN 80 in cyclohexane, and presaturated with compound (I), is prepared. The dispersant solution is filtered through a 0.2 micron microporous membrane filter to provide a particle-free dispersant solution. The sample then is added to the dispersant solution until an acceptable level of laser light obscuration is achieved, at which point the particle size distribution is measured.

Triplicate measurements are effected as a minimum a) to provide more reliable measurements and b) to check the equivalent sampling of the suspended material. The results are automatically recorded and displayed graphically to give a cumulative % undersize vs. diameter and a frequency percentage vs. diameter for the sample. From this, the d90 equivalent spherical volume diameter value is derived (90% cumulative undersize value).

The compound of structural formula (I) in a free particulate form within the above-mentioned limits, then can be mixed with excipients, diluents, or carriers as necessary to provide, for example, dry powders, aerosols, suspensions, suspension or solid filled capsules, and compressed tablets as oral dosage forms of compound (I).

The particle size of free compound (I) in a pharmaceutical composition also can be determined. For example, it is envisioned that the d90 particle size of compound (I) can be determined either in a formulated dosage form or as particles of the free drug, by a microscopic method. First, the composition is separated into its individual components, or at least compound (I) is separated from the composition. Persons skilled in the art are aware of separation techniques that maintain the particle size of compound (I) during separation of compound (I) from the composition. For example, water-soluble constituents of the composition can be dissolved in water, leaving the highly water insoluble particles of compound (I) without altering the particle size of compound (I) particles.

The undissolved particles then can be examined under a microscope. The crystalline compound (I) can be visually differentiated from amorphous composition ingredients. The particle size of compound (I) is determined by visual inspection and by comparison to standardized particles of a known size. To ensure that the particle size of compound (I) particles is being determined, an infrared microprobe can be used to assay the particles and confirm their identity as compound (I).

Any pharmaceutically acceptable excipients can be used to formulate tablets. The tablets typically contain about 1 to about 20 mg of compound (I). Thus, for example, the particulate compound (I) can be mixed with generally recognized as safe pharmaceutical excipients, including liquid diluents, solid diluents (preferably water-soluble diluents), wetting agents, binders, disintegrants, and lubricants. See, e.g., Handbook of Pharmaceutical Excipients 2nd Edition, Amer. Pharm. Assoc. (1994). Preferred solid excipients include lactose, hydroxypropylcellulose, sodium lauryl sulfate, microcrystalline cellulose, talc, colloidal silicon dioxide, starch, magnesium stearate, stearic acid, and croscarmellose sodium. Liquid excipients include, for example, propylene glycol, glycerin, and ethanol. The pharmaceutical compositions are prepared by standard pharmaceutical manufacturing techniques, as described in Remington's Pharmaceutical Sciences, 18th Ed. (1990), Mack Publishing Co., Easton, Pa. Such techniques include, for example, wet granulation followed by drying, milling and compression into tablets with or without film coating; dry granulation followed by milling, compression into tablets with or without film coating; dry blending followed by compression into tablets, with or with film coating; molded tablets; sachets; suspensions; wet granulation, dried and filled into gelatin capsules; dry blend filled into gelatin capsules; or suspension filled into gelatin capsules. Generally, solid compositions have identifying marks that are debossed or imprinted on the surface. The total active ingredients in such pharmaceutical compositions comprises from 0.1% to 99.9%, preferably about 1 to 10% by weight of the composition. Preferably, the relative weight percent of excipients is as follows:

|  | Quantity (% by weight) |
|---|---|
| Compound (I) | 1 to 6 |
| Lactose (diluent) | 50 to 75 |
| Hydroxypropylcellulose (binder/diluent) | 1 to 5 |
| Croscarmellose Sodium (disintegrant) | 3 to 10 |
| Sodium Lauryl Sulfate (wetting agent) | 0 to 5 |
| Microcrystalline Cellulose (diluent/disintegrant) | 5 to 50 |
| Magnesium Stearate (lubricant) | 0.25 to 2.0 |

The specific dose of compound (I) administered according to this invention is, of course, determined by the particular circumstances surrounding the case including, for example, the route of administration, the state of being of the patient, and the pathological condition being treated. A typical daily dose contains a nontoxic dosage level from about 1 to about 20 mg/day of compound (I). Preferred daily doses generally are about 1 to about 20 mg/day, particularly 5 mg, 10 mg, and 20 mg tablets, administered as needed.

The compositions of this invention can be administered by a variety of routes suitable for particulate dosage forms and are preferably administered orally. These compounds preferably are formulated as pharmaceutical compositions prior to administration. The selection of dose is decided by the attending physician.

A compound (I)/hydroxypropylmethylcellulose phthalate coprecipitate was manufactured generally by the method set forth in Butler U.S. Pat. No. 5,985,326. After preparation of coprecipitate, the coprecipitate was milled to provide particles having a relatively large particle size and a relatively wide particle size distribution, i.e., d50=200 microns. The coprecipitate there was subjected to a controlled dissolution at a pH that ordinarily would not release compound (I) from the polymeric coprecipitate component. Applicants found that the coprecipitate contained a portion of the free drug form of compound (I) not embedded in the coprecipitate polymer. In clinical studies (see Example 2), applicants further discovered that the blood levels of compound (I) within thirty minutes of administration was attributable to the free drug present in the coprecipitate compositions.

These results are surprising in view of Butler U.S. Pat. No, 5,985,326 which is directed to a method of preparing a solid dispersion of compound (I) as coprecipitate. The disclosed process and coprecipitate of Butler U.S. Pat. No. 5,985,326 is directed to providing a solid dispersion of a poorly water-soluble drug, which has an enhanced bioavailability compared to free particles of the poorly water-soluble drug. Butler U.S. Pat. No. 5,985,326 therefore is attempting to avoid the free form of the drug. Butler U.S. Pat. No. 5,985,326 generally discloses milling of the coprecipitate, but fails to disclose the size of the coprecipitate particles after milling, and especially fails to disclose either the presence of the free drug form of compound (I) or, if present, a particle size of the free drug form of compound (I).

Based on these observations, it was concluded that a bimodal delivery of compound (I) could be achieved with a rapid delivery of the free drug followed by a slower delivery of the drug upon the pH sensitive release from the polymeric coprecipitate particles. These observations, in turn, gave rise to the possibility that rapid drug delivery could be effected by compositions incorporating compound (I) entirely in free drug form, provided that suitable stability could be achieved and that the particle size of the drug is controlled in a well-defined range for manufacture of the composition. Accordingly, compound (I) in the pharmaceutical compositions of the present invention preferably is comprised entirely of free drug in particulate form, but alternatively the composition can contain a combination of free drug in particulate form and an embedded drug form to provide a bimodal drug delivery. Preferably, the free drug constitutes greater than 75% free drug (most preferably, greater than 90% free drug) of compound (I) in such compositions.

In one embodiment of the present invention, the free drug form of compound (I), and pharmaceutically-acceptable excipients, diluents, and carriers, are present in a pharmaceutical composition that exhibits a $C_{max}$ (i.e., the maximum observed plasma concentration of compound (I)) of about 180 to about 280 μg/L (micrograms/liter), or an AUC (0–24) (i.e., the area under the plasma concentration curve from zero to twenty-four hours) of about 2280 to about 3560 μg·h/L (microgram·hour/liter), measured using a 10 mg dose of the compound. In a preferred embodiment, the composition exhibits a $C_{max}$ of about 180 to about 280 μg/L and an AUC of about 2280 to about 3650 μg·h/L, measured using a 10 mg dose of the compound. In this embodiment, the composition can be a solid, e.g., a tablet or powder, by using solid diluents, carriers, and/or excipients, or a suspension, e.g., encapsulated in a soft gel, or a solution by using liquid carriers, diluents, and/or carriers.

The $C_{max}$ and AUC (0–24) were determined by analyzing for compound (I) in plasma using a validated LC/MS/MS method, with a lower limit of quantitation of 0.5 ng/mL. The analytes and an internal standard i.e., the $[^{13}C][^2H_3]$ isotope of compound (I), were extracted from the plasma by solid phase extraction with 3 mL Empore SD C2 cartridges using 150 µL of 90:10 methanol:water. The analytes were separated using high performance liquid chromatography with a Penomenex Luna phenylhexyl (4.6 mm×100 mm, 5µ) column with a water: acetonitrile (10:90) mobile phase at 1.0 mL/minute. Detection was performed using a Perkin Elmer Sciex API III Plus tandem mass spectrometer using atmospheric pressure chemical ionization (APCI) in positive ion mode.

It should be understood that $C_{max}$ and AUC (0–24) in plasma is dose dependent. For example, a composition containing a 20 mg dosage of compound (I) will exhibit a $C_{max}$ and AUC (0–24) about twice that of a composition containing a 10 mg dosage. Similarly, a composition containing a 5 mg dosage of compound (I) will exhibit a $C_{max}$ and AUC (0–24) of about one-half that of a composition containing a 10 mg dosage.

Accordingly, the present invention encompasses, for example, compositions containing a 20 mg dosage of compound (I) exhibiting a $C_{max}$ of about 360 to about 560 µg/L and/or an AUC (0–24) of about 4560 to about 7120 µg·h/L; and a composition containing a 5 mg dosage of compound (I) exhibiting a $C_{max}$ of about 90 to about 140 and/or an AUC (0–24) of about 1140 to about 1780 µg·h/L. Persons skilled in the art are aware of techniques in which the $C_{max}$ and AUC (0–24) of compositions containing a dosage of compound (I) different from 10 mg can be compared or standardized to the $C_{max}$ and AUC (0–24) of a composition containing a 10 mg dose of compound (I).

In another embodiment, a composition containing compound (I), either as the free drug alone or as the free drug admixed with a coprecipitate of compound (I), and pharmaceutically-acceptable excipients, diluents, and carriers, exhibits a $C_{max}$ about 180 to about 280 µg/L and an AUC (0–24) of about 2280 to about 3650 µg·h/L. In this embodiment, the composition can be a solid or a suspension.

Yet another embodiment of the present invention is a pharmaceutical composition containing a therapeutically-effective amount of particles of compound (I) and pharmaceutically-acceptable carriers, diluents, and excipients, wherein at least 90% of the particles of compound (I) have a particle size of less than about 10 microns, and bioequivalent compositions thereof. The term "bioequivalent compositions" is defined herein as a composition having a $C_{max}$ of about 180 to about 280 µg/L, and an AUC (0–24) of about 2280 to about 3560 µg·h/L, measured using a 10 mg dose of particles of compound (I) having a d90=10 and a human test subject.

$C_{max}$ and AUC (0–24) be determined by methods well-known to person skilled in the art using humans, primates, dogs, rabbits, or rodents (e.g., rats, mice, guinea pigs, and hamsters), for example, as test subjects for bioequivalence. Preferred test animals are humans and dogs.

The present invention will be more readily understood upon consideration of the following illustrative examples wherein: Example 1 relates to in vitro solubility characteristics of the free drug form of compound (I) of varying particle size; Examples 2 and 3 relate to in vivo tests of pharmaceutical compositions incorporating a particulate form according to the invention in comparison to compositions incorporating a coprecipitate and in comparison to compound (I) of a relatively large particle size; and Examples 4 and 5 relate to pharmaceutical compositions employing particulate free drug according to the invention in differing dosage strengths.

EXAMPLE 1

In vitro dissolution tests were performed using compound (I) which had been processed by milling from its raw state particulate form (d90=75–200 microns) into particulate preparations having d90 (microns) values as follows: Lot 1, d90=4; Lot 2, d90=22; Lot 3, d90=55; Lot 4, d90=65; Lot 5, d90=73; and Lot 6, d90=116. Alternative milling technologies were employed to develop the various lots. For example, Lot 1 was made using a 12 inch pancake style jet mill fed at a rate of 28–30 kg/hour with sufficient grind pressure to produce the d90=4 material. Lot 2 was prepared in an Alpine VPZ-160 universal mill equipped with pin discs (stud plates) and run at approximately 10,000 rpm.

Lots were evaluated in vitro by accurately weighing approximately 10 mg of bulk drug into a test tube, adding 1 mL of purified water, and sonicating for up to 2 minutes to ensure the powder was wetted. The drug slurry was subsequently transferred to a dissolution apparatus vessel containing 1000 mL of aqueous 0.5% sodium lauryl sulfate at 37° C. The test tube was rinsed with multiple aliquots of warmed dissolution medium and added back into the dissolution vessel. The paddle speed was 50 rpm and samples were taken at 5, 10, 20, and 30 minutes and subsequently analyzed by HPLC. The results are illustrated in FIG. 1 and demonstrate improved in vitro dissolution occurs with smaller particle sizes of compound (I).

EXAMPLE 2

The improvement in bioavailability and reproducibility of pharmaceutical compositions made available by the present invention is demonstrated in vivo in humans. The following Table 1 demonstrates the pharmaceutical compositions prepared as in Examples 4 and 5 with particulate free drug having a d90 of 8.4 microns compared to composition incorporating the coprecipitate of compound (I) with hydroxypropylmethylcellulose phthalate (coprecipitate). In each instance, the tableted composition was designed to deliver a 10 mg dose of compound (I).

TABLE 1

| In vivo evaluation | | |
|---|---|---|
| Pharmaceutical Composition | No. of Patients | $T_{max}$ (hrs) |
| Free Drug of Compound (I) | 18 | 2.0 |
| Coprecipitate of Compound (I) | 18 | 3.5 |

The composition incorporating a particulate free drug form having a d90 of 8.4 demonstrated significantly improved $T_{max}$ over a composition containing the coprecipitate ($T_{max}$ is a measure of the time to achieve peak blood levels of a drug, and is indicative of improved onset of action). The particulate free drug formulation correspondingly provided a more rapid rate of absorption of compound (I) into plasma, providing a geometric mean plasma level at 30 minutes of 51 ng/ml (nanograms per milliliter)as compared to 29 ng/ml for the coprecipitate formulation.

EXAMPLE 3

A study was conducted to determine the bioequivalence of tablets containing compound (I) in different particle sizes. The tablets contained compound (I) in a particle size of d90=8.4µ (micron), d90=20µ, or d90=52 µ.

The study was an open-label, randomized, three-period crossover study conducted on twenty-four (24) healthy male subjects aged 18 to 65 years old, divided into two groups of twelve. A single 10 mg oral dose was administered with 180 mL of water in each of three treatment periods, and the pharmacokinetics of tablets containing compound (I) in different particle sizes were compared.

After dosing, the subjects underwent pharmacokinetic blood sampling. There was an interval of at least 10 days between dosing in each treatment period to eliminate any residual compound (I) from the previous treatment period. The post-study assessment was conducted between 7 and 14 days after the final dosing.

Compound (I) was absorbed relatively quickly following oral dosing from the d90=52, 30, and 8.4µ particle size formulations. However, the rate and extent of absorption of compound (I) increased with decreasing particle size. A comparison of $C_{max}$ and AUC (0–24) data showed that the difference in absorption between particle size formulations was most apparent over the first 24 hours after dosing. As used herein, $C_{max}$ is defined as the maximum observed plasma concentration of compound (I), and AUC (0–24) is defined as the area under the plasma concentration time curve from zero to twenty-four hours. Both $C_{max}$ and AUC (0–24) are well-known and understood variables to persons skilled in the art.

With respect to $C_{max}$ the d90=52µ and d90=20µ formulations were not bioequivalent to the d90=8.4µ formulation because the 90% confidence interval (CI) was outside of the 0.8 to 1.25 equivalence limits. In particular, $C_{max}$ was 36% and 23% lower for the 52µ and 20µ formulations, respectively, compared to the 8.4µ formulation. The 52µ formulation also was not equivalent to the 8.4µ formulation with respect to AUC (0–24), which was 23% lower than the 8.4µ formulation. The 20µ and 8.4µ formulations were bioequivalent with respect to AUC (0–24). The 8.4µ, 20µ, and 52µ formulations were bioequivalent with respect to AUC, i.e., the area under the plasma concentration time curve from time zero to infinity.

The study showed that the rate of absorption of compound (I), based on $C_{max}$ and $t_{max}$ (i.e., time to attain maximum observed drug-plasma concentration), was slower for the 52µ formulations in relation to the 8.4µ formulation. As stated above, $C_{max}$ was not equivalent for the 52µ and 20µ formulations compared to the 8.4µ formulation. Median $t_{max}$ occurred one hour later for the 52µ formulation, but was similar to the 20µ and 8.4µ formulations.

The following table summarizes various pharmacokinetic parameters of compound (I) following oral administration of a single 10 mg dose of the d90 52µ, 20µ, and 8.4µ particle size formulations.

|  | d90 = 52µ | d90 = 20µ | d90 = 8.4µ |
|---|---|---|---|
| $C_{max}$ (µg/L) | 142 | 189 | 224 |
| $t_{max}$ (h)[1] | 3.00 | 2.00 | 2.00 |
| AUC (0–24)[2] | 2201 | 2667 | 2849 |

[1] median data.
[2] in micrograms · hour/liter.

This study showed that reducing the particle size of compound (I) in accordance with the present invention has an impact on the in vivo rate of absorption of compound (I) from a solid dosage form, and, hence, on the bioavailability of compound (I). For example, from the statistical analysis, $t_{max}$ for the 52µ formulation occurred significantly (i.e., 1 hour) later than for the 8.4µ formulation. There was no significant difference in $t_{max}$ between the 20µ and 8.4µ formulations. Accordingly, onset of a therapeutic benefit attributed to compound (I) after administration is significantly faster for the 8.4µ and 20µ formulations compared to the 52µ formulation.

In addition to dissolution and in vivo absorption, another important aspect of the physical properties of particulate β-carboline preparations according to the present invention is the impact on the various unit operations of the drug product manufacturing process. While the particle size specification ensures consistent delivery of the drug molecule to the sites of absorption in the gastrointestinal tract, it also imparts better control during the tablet manufacturing process.

The following formulation examples are illustrative only and are not intended to limit the scope of the present invention.

EXAMPLE 4

The following formula was used to prepare the finished dosage form of a tablet providing 10 mg of compound (I).

| Ingredient | Quantity (mg) |
|---|---|
| Granulation | |
| Compound (I) (Lot 1, d90 of 4) | 10.00 |
| Lactose Monohydrate | 153.80 |
| Lactose Monohydrate (Spray Dried) | 25.00 |
| Hydroxypropylcellulose (EF Extra Fine) | 4.00 |
| Croscarmellose Sodium | 9.00 |
| Hydroxypropylcellulose (EF) | 1.75 |
| Sodium Lauryl Sulfate | 0.70 |
| Outside Powders | |
| Microcrystalline Cellulose (Granular-102) | 37.50 |
| Croscarmellose Sodium | 7.00 |
| Magnesium Stearate (Vegetable) | 1.25 |
| Total | 250 mg |

Purified Water, USP was used in the manufacture of the tablets. The water was removed during processing and minimal levels remained in the finished tablets.

Tablets are manufactured using a wet granulation process. A step-by-step description of the process follows. Compound (I) and excipients to be granulated are security sieved. Compound (I) is dry blended with lactose monohydrate (spray dried), hydroxypropylcellulose, croscarmellose sodium, and lactose monohydrate. The resulting powder blend was granulated with an aqueous solution of hydroxypropylcellulose and sodium lauryl sulfate using a Powrex or other suitable high shear granulation. Additional water can be added to reach the desired endpoint. A mill can be used to delump the wet granulation and facilitate drying. The wet granulation was dried using either a fluid bed dryer or a drying oven. After drying, the material can be sized to eliminate any large agglomerates. Microcrystalline cellulose, croscarmellose sodium, and magnesium stearate were security sieved and added to the dry sized granules. These excipients and the dry granulation were mixed until uniform using a tumble bin, ribbon mixer, or other suitable mixing equipment. The mixing process can be separated into two phases. The microcrystalline cellulose, croscarmellose sodium, and the dried granulation were added to the mixer and blended during the first phase, followed by the addition of the magnesium stearate to this granulation and a second mixing phase.

The mixed granulation then was compressed into tablets using a rotary compression machine. The core tablets were film coated with an aqueous suspension of the appropriate color mixture in a coating pan (e.g., Accela Cota). The coated tablets can be lightly dusted with talc to improve tablet handling characteristics.

The tablets are filled into plastic containers (30 tablets/container) and accompanied by package insert describing the safety and efficacy of the formulation.

EXAMPLE 5

By analogous procedures, the following formula was used to prepare the finished dosage form of a tablet providing 5.0 mg and 20 mg of compound (I).

| Ingredient | Quantity (mg) | Quantity (mg) |
|---|---|---|
| Granulation | | |
| Compound (I) (Lot 1, d90 of 4) | 5.00 | 20.00 |
| Lactose Monohydrate | 109.66 | 210.19 |
| Lactose Monohydrate (Spray Dried) | 17.50 | 35.00 |
| Hydroxypropylcellulose | 2.80 | 5.60 |
| Croscarmellose Sodium | 6.30 | 12.60 |
| Hydroxypropylcellulose (EF) | 1.22 | 2.45 |
| Sodium Lauryl Sulfate | 0.49 | 0.98 |
| Outside Powders | | |
| Microcrystalline Cellulose (Granular-102) | 26.25 | 52.50 |
| Croscarmellose Sodium | 4.90 | 9.80 |
| Magnesium Stearate (Vegetable) | 0.88 | 0.88 |
| Total | 175 mg | 350 mg |

The principles, preferred embodiments, and modes of operation of the present invention have been described in the foregoing specification. The invention that is intended to be protected herein, however, is not construed to be limited to the particular forms disclosed, because they are to be regarded as illustrative rather than restrictive. Variations and changes may be made by those skilled in the art without departing from the spirit of the invention.

What is claimed is:

1. A free drug particulate form of a compound having a formula

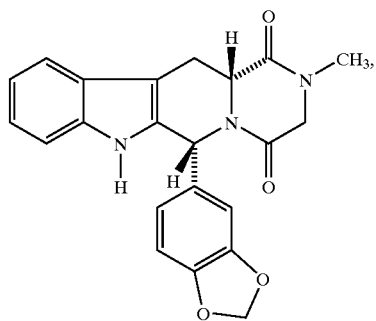

or pharmaceutically acceptable salts and solvates thereof, comprising particles of the compound wherein at least 90% of the particles have a particle size of less than about 40 microns.

2. The free drug particulate form of claim 1 wherein at least 90% of the particles have a particle size of less than about 25 microns.

3. The free drug particulate form of claim 1 wherein at least 90% of the particles have a particle size of less than about 15 microns.

4. The free drug particulate form of claim 1 wherein at least 90% of the particles have a particle size of less than about 10 microns.

5. A pharmaceutical solid composition comprising the free drug particulate form as in any one of claims 1–4 and one or more pharmaceutically-acceptable carriers, diluents, or excipients.

6. A method of treating sexual dysfunction in a patient in need thereof, which comprises administering to the patient a therapeutically effective amount of a solid composition comprising the free drug particulate form as in any one of claims 1–4 and one or more pharmaceutically-acceptable carriers, diluents, or excipients.

7. The method of claim 6 wherein the sexual dysfunction is male erectile dysfunction.

8. The method of claim 6 wherein the sexual dysfunction is female sexual arousal disorder.

9. A method of manufacturing the free drug particulate form of claim 1 comprising:
   (a) providing a solid, free form of the compound, and
   (b) comminuting the solid free form of the compound to provide particles of the compound wherein at least 90% of the particles have a particle size of less than about 40 microns.

10. The method of claim 9 further comprising the step of admixing the particles of step (b) with one or more pharmaceutically-acceptable carriers, diluents, or excipients.

11. A pharmaceutical solid composition prepared by admixing particles of a compound having a formula

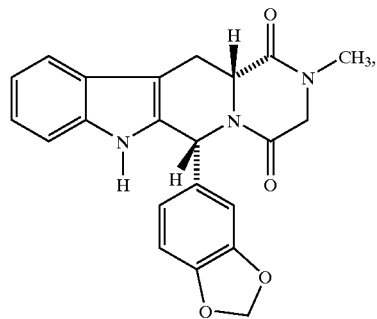

or a pharmaceutically acceptable salt or solvate thereof, with one or more pharmaceutically acceptable carrier, diluent, or excipient, wherein the particles of the compound have a d90=40 or less.

* * * * *

UNITED STATES PATENT AND TRADEMARK OFFICE
CERTIFICATE OF CORRECTION

PATENT NO. : 6,821,975 B1
DATED : November 23, 2004
INVENTOR(S) : Anderson et al.

It is certified that error appears in the above-identified patent and that said Letters Patent is hereby corrected as shown below:

Column 1,
Line 67, "5-carboline" should be -- β-carboline --

Column 2,
Line 57, "dysfunction" should be -- dysfunction. --

Column 3,
Line 32, "micrograms" should be -- microgram • --
Line 44, "form the following description" should be -- from the following description --

Column 4,
Line 39, "6.1" should be -- 6,1 --
Line 41, "formula" should be -- formula (I): --
Line 56, after structure, please add -- (I), --

Column 5,
Line 47, "raw 5 state" should be -- raw state --

Column 6,
Line 24, "contro" should be -- control --

Column 9,
Line 54, "be determined" should be -- can be determined --

Column 11,
Line 28, "$C_{max}$" should be -- $C_{max}$, --

Signed and Sealed this

Third Day of May, 2005

JON W. DUDAS
*Director of the United States Patent and Trademark Office*